United States Patent [19]

Royall et al.

[11] Patent Number: 5,426,217
[45] Date of Patent: Jun. 20, 1995

[54] PROCESS FOR THE PRODUCTION OF THEREPHTHALIC ACID

[75] Inventors: David J. Royall, Guisborough; James L. Harvie, Middlesbrough, both of England

[73] Assignee: Imperial Chemical Industries, PLC, London, England

[21] Appl. No.: 1,548

[22] Filed: Jan. 6, 1993

[30] Foreign Application Priority Data

Jan. 7, 1992 [GB] United Kingdom ............... 9200176

[51] Int. Cl.$^6$ ............................................. C07C 51/487
[52] U.S. Cl. ..................................... 562/483; 562/485; 562/487; 568/858; 568/868
[58] Field of Search ................ 562/483, 485, 487; 568/858, 868

[56] References Cited

U.S. PATENT DOCUMENTS

| 4,578,510 | 3/1986 | Doerr | 562/483 |
| 4,620,032 | 10/1986 | Doerr | 502/483 |
| 5,095,145 | 3/1992 | Rosen | 562/483 |

FOREIGN PATENT DOCUMENTS

| 14854 | 6/1958 | Germany . |
| 1130695 | 10/1968 | United Kingdom . |
| 2123403 | 2/1984 | United Kingdom . |

Primary Examiner—José G. Dees
Assistant Examiner—Samuel Barts
Attorney, Agent, or Firm—Cushman, Darby & Cushman

[57] ABSTRACT

A process for the production of terephthalic acid comprises subjecting polyalkylene terephthalate to hydrolysis using a ratio of water to polyalkylene terephthalate in the mixture prior to heating and carrying out the reaction under conditions such that, at the reaction temperature, a significant proportion of the terephthalic acid produced is in the solid phase. The degree of recrystallization necessary to recover the terephthalic acid produced is thereby reduced. The reaction can with advantage be carried out with alkylene glycol present in the mixture prior to hydrolysis.

34 Claims, No Drawings

PROCESS FOR THE PRODUCTION OF THEREPHTHALIC ACID

This invention relates to a process for the production of terephthalic acid and in particular to a process for the production of terephthalic acid by hydrolysis of polyalkylene terephthalate for example polyethylene terephthalate (PET).

It is known that terephthalic acid which is suitable for polymerisation with alkylene glycols either directly or after purification my be obtained by the hydrolysis of waste polyalkylene terephthalate.

GA-213403 discloses a continuous procedure for obtaining pure terephthalic acid from PET waste in which the PET waste is heated in water and in which process the presence of decolourising carbon in the water is essential. Additionally, this procedure utilises sufficient water, and is operated at such a temperature, that the terephthalic acid product dissolves in the water as it is produced to form an aqueous solution of terephthalic acid, there being substantially no terephthalic acid in the solid phase, which solution is subsequently filtered to remove the carbon: the terephthalic acid is then crystallised from the filtrate.

It is also known from East German Patent No. 14854 to produce terephthalic acid by hydrolysis of PET. In this case, the teaching also appears to be directed towards producing the terephthalic acid product in solution at the reaction conditions employed. The disclosure refers to filtering the hot reaction solution under pressure using a filter which can trap both colouring and mechanical impurities. The hot solution is thereafter cooled to crystallise the terephthalic acid which is then isolated and dried.

U.S. Pat. No. 5095145 is likewise concerned with effecting depolymerisation of waste PET products by depolymerisation there of in an aqueous mixture at a temperature within the range 430° to 600° F. to produce an aqueous crude terephthalic acid solution which is thereafter processed further.

According to one aspect of the present invention there is provided a process for the production of terephthalic acid from polyalkylene terephthalate, comprising heating a mixture of a solid material containing polyalkylene terephthalate and an aqueous medium to effect hydrolysis of the polyalkylene terephthalate and thereby produce terephthalic acid, the ratio of water to polyalkylene terephthalate in the mixture prior to heating and the conditions under which the hydrolysis reaction is carried out being such that, at the reaction temperature, at least 10% of the terephthalic acid produced is in the solid phase.

We have surprisingly found that advantages may be secured by hydrolysing polyalkylene terephthalate in aqueous medium to produce terephthalic acid and ethylene glycol under conditions in which at least part of the terephthalic acid produced is in the solid phase.

The process of the present invention provides at least part of the terephthalic acid as a solid material in the aqueous medium rather than as a product which is completely dissolved in the said medium and therefore less recrystallisation is necessary to recover it from the aqueous medium as compared with the processes of the prior art. Furthermore, the process of the present invention provides the advantage that the particle size of the terephthalic acid product can be controlled in order to facilitate subsequent separation from other larger particles such as unreacted materials for example PVC which, as described hereinafter, may be present in the polyalkylene terephthalate containing material. Moreover, to obtain a substantial amount of the terephthalic acid in the solid phase under the reaction conditions requires a relatively large ratio of polyalkylene terephthalate to water in the mixture prior to heating and, as a result, a relatively concentrated solution of alkylene glycol in the aqueous liquor is obtained following the hydrolysis reaction which leads to correspondingly less water to remove in order to recover the alkylene glycol. The costs of such recovery are thus reduced.

The polyalkylene terephthalate may be in any suitable form although it is preferred that the polyalkylene terephthalate is in the form of particles such as granules or flakes. PET bottles provide a major source of PET suitable for recycling to produce terephthalic acid although it may be desirable to separate the PET from any other plastics materials contained in the bottles such as polyvinylchloride (PVC) prior to hydrolysis.

Suitably the aqueous medium is demineralised water thus reducing the possibility of competing reactions reducing the yield of terephthalic acid but other polar solvents such as alkylene glycols for example ethylene glycol may be present if desired. The aqueous medium may comprise at least 85% by weight demineralised water, often at least 90%, and in some instances substantially pure, demineralised water.

The polyalkylene terephthalate to be hydrolysed may be added to the aqueous medium by any suitable means. Suitably the amount of polyalkylene terephthalate to be hydrolysed in the aqueous medium is at least 15%, typically 25 to 80%, and desirably 30 to 60% by weight of the polyalkylene terephthalate based on the combined weight of the polyalkylene terephthalate and water in the aqueous medium. The larger the proportion of polyalkylene terephthalate in the solution the greater the processing capacity: however this proportion is limited by the stoichiometric requirements of the hydrolysis of polyalkylene terephthalate, that is, 2 moles of water are required to produce 1 mole of alkylene glycol and 1 mole of terephthalic acid in the hydrolysis of polyalkylene terephthalate.

At least 20%, more usually at least 30% (and preferably a much higher proportion), of the total amount of terephthalic acid produced in the hydrolysis is produced as a solid material, the remaining terephthalic acid produced being in solution.

As mentioned previously, alkylene glycol may be present in the mixture prior to hydrolysis. This is advantageous in simplifying recovery of the glycol following the reaction since the proportion of glycol present relative to water is enhanced.

Accordingly, in another aspect of the present invention there is provided process for the production of terephthalic acid from polyalkylene terephthalate, comprising: heating a mixture of a solid material containing polyalkylene terephthalate, water and alkylene glycol to effect hydrolysis of the polyalkylene terephthalate and thereby produce terephthalic acid, the ratio of water to polyalkylene terephthalate in the mixture prior to heating and the conditions under which the hydrolysis reaction is carried out being such that, at the reaction temperature, at least 30% of the terephthalic acid produced is in the solid phase; separating terephthalic acid from the aqueous liquor remaining following the hydrolysis reaction; and processing the remaining liquor to separate therefrom alkylene glycol present in the mixture prior to the hydrolysis reaction together with alkylene glycol derived from hydrolysis of the polyalkylene terephthalate.

In addition to facilitating subsequent separation of the glycol from water, the addition of glycol prior to hydrolysis is advantageous in that the excess glycol present serves to dissolve any oligomers which are not fully depolymerised during the hydrolysis reaction thereby facilitating separation of terephthalic acid from such oligomers.

It is preferred that as much as possible of the terephthalic acid produced is in the solid phase as this reduces the amount of recrystallisation required to recover any terephthalic acid in solution. Thus, the amount in the solid phase is advantageously at least 70%, and especially at least 80%, of the total amount of terephthalic acid produced in the hydrolysis reaction.

Usually the alkylene moiety in the polyalkylene terephthalate corresponds to that in the glycol, the preferred alkylene being ethylene.

Typically the alkylene glycol content of the mixture prior to the hydrolysis reaction is at least 5%, more usually at least 10%, by weight of the liquid phase present; preferably the alkylene glycol content is at least 15%, more preferably at least 20%, by weight of the liquid phase present.

The mixture of polyalkylene terephthalate and the aqueous medium is suitably heated in an autoclave to a temperature of at least 190° C. and not exceeding 300° C., desirably 200° to 270° C. and optimally to 220° to 240° C. Hydrolysis at lower temperatures than 190° C. may be employed if desired; however, in order to secure a similar yield of terephthalic acid to that obtained at a temperature of at least 190° C., the reaction time must be increased significantly.

A feature of the invention is that the formation of terephthalic acid in the solid phase during the hydrolysis reaction results in a relatively small particle size and also allows particle size to be controlled at this stage. Thus, according to a preferred feature thereof, the process of the present invention includes controlling the nature of particle formation during the hydrolysis reaction. More specifically, particle formation is preferably controlled in such a way that the particles of solid phase terephthalic acid particles forming during the hydrolysis reaction are of rounded shape, desirably such that at least 90% of the particles of the recovered solid phase terephthalic acid are sufficiently small to pass through a sieve having a grid size 2 mm, preferably 1 mm, more preferably 800 microns, and especially 500 microns square.

Thus, by controlling the particle size during the hydrolysis reaction, it becomes possible to achieve a desired particle size and distribution consistent with the requirements imposed by subsequent processing of the terephthalic acid product, without the necessity for a separate processing vessel (eg crystalliser) for treating the terephthalic acid in order to obtain the desired particle size and distribution. Various ways of controlling particle size can be contemplated such as control of the temperature gradient within the reaction vessel and/or the provision of surfaces which promote formation of the desired particle shape and size. One particularly effective control techique is to effect agitation of the reaction mixture during hydrolysis, for example by means of stirring. Agitation may be continued after the hydrolysis reaction has been completed and during cooling of the reaction mixture so as to promote crystallisation of terephthalic acid which has remained in solution in the form of rounded particles (as opposed to needle-shaped particles typically of the order of 1 cm in length as tends to happen if the solution is allowed to cool naturally).

Preferably therefore, the reaction mixture is suitably agitated during heating. By suitably controlling particle size formation from the reaction mixture, for instance by agitation of the reaction mixture, it is possible to secure that at least 90% of terephthalic particles recovered are of rounded shape capable of passing a sieve having a square grid size of 2 mm (more preferably 1 mm and even more preferably 500 microns), as opposed to needle-shaped particles, which is advantageous not only in terms of facilitating separation from somewhat larger particles of, for example, PVC but is also advantageous when the particles are subsequently slurried with alkylene glycol in the course of PET production since particle packing density is of importance in this respect.

Desirably, the hydrolysis is conducted at a temperature and for sufficient time to provide a yield of terephthalic acid of at least 70%, preferably at least 90%, especially at least 95% for example at least 98 mole % based on the moles of terephthalate units in the polyalkylene terephthalate.

The rate of hydrolysis of polyalkylene terephthalate increases with temperature. However, residual impurities for example PVC may lead to an undesirable increase in the colour of the terephthalic acid product when produced at higher temperatures and it is therefore highly desirable to select an optimum reaction temperature at which the rate of reaction is sufficiently high and the level of colour in the terephthalic acid product is acceptably low.

The pressure at which hydrolysis may be carried out is determined by the temperature of the reaction in a closed vessel but is preferably conducted at elevated pressure.

Conveniently, in order to avoid undesirable oxidation, the hydrolysis is carried out in the absence of molecular oxygen and suitably under a blanket of an inert gas for example nitrogen.

The hydrolysis is suitably carried out for sufficient time to provide the desired degree of hydrolysis and is preferably up to 5 hours, more preferably 10 minutes to 3 hours and especially 30 minutes to 2 hours. The period over which hydrolysis is carried out may also depend on the particular form of polyalkylene terephthalate to be hydrolysed.

The terephthalic acid produced in the solid phase may be separated from the aqueous medium conventionally for example by filtration to provide terephthalic acid which is substantially free of impurities. Impurities which may be present during the hydrolysis include polyvinyl chloride and metal residues contained in the polyalkylene terephthalate which may be for example residues derived from the polymerisation catalyst employed in the production of the polyalkylene terephthalate. Soluble metal impurities may be separated from the terephthalic acid by employing a hot filtration in which the terephthalic acid is retained by the filter and metal impurities are suitably carried through the filter into the filtrate.

Typically said hot filtration is carried out at a temperature of at least 60° C., more preferably at least 70° C., a suitable range being from about 80° to about 150° C.

Following said hot filtration step, the recovered terephthalic acid is preferably subjected to at least one hot wash followed by filtration. For instance, the recovered terephthalic acid may be reslurried in fresh water and heated to effect a hot wash. Glycol may also with advantage be incorporated in the hot wash in order to facilitate stripping from the recovered terephthalic acid oligomers formed during the hydrolysis reaction. The hot washed terephthalic acid/water is then subjected to filtration to separate the terephthalic acid. Hot washing in this manner has been found to enhance removal of impurities, especially yellow colour formers.

Hot washing is typically carried out at a temperature of at least 60° C. more preferably at least 70° C., a suitable range being from about 80° C. to about 150° C.

Desirably the polyalkylene terephthalate to be hydrolysed is substantially free of impurities such as PVC as the hydrolysis conditions may also lead to degradation of a proportion of the PVC producing an undesirable chlorine residue in the solution which may lead to corrosion in the hydrolysis reactor. However, if such a chlorine residue is produced, whilst being potentially detrimental to the hydrolysis reactor as regards corrosion, it tends to remain in solution and not be incorporated in the terephthalic acid produced to any significant extent.

As the terephthalic acid particle size is small, it may be separated from any particulate PVC impurities by drying the mixture and then sieving it, the terephthalic acid passing through the sieve and the PVC being retained by it.

Alternatively, instead of separating contaminants such as particulate PVC impurities from the terephthalic acid following drying of the latter, the PVC or other particulate contaminants may be separated out at an earlier stage during the process.

The process of the present invention may be operated in batch mode but is preferably operated in continuous mode.

The hydrolysis reaction may be carried out in stages in both the batch and continuous modes of operation. For instance, the hydrolysis reaction my be carried out in two stages: a first stage in which the hydrolysis conditions are relatively mild (eg at a temperature within the range of 190° to 210° C. followed by transfer of the reaction mixture to a second stage in which the hydrolysis conditions are more severe (for example at a temperature of 200° C. and greater, typically 220° to 240° C.). In this event, transfer of the reaction mixture from the first stage to the second stage my involve one or more separation stages in which, for example, particulate impurities such as PVC particles are separated from the reaction mixture before subjecting the latter to more severe hydrolysis conditions. Also, the solid phase terephthalic acid formed during the first stage may, if desired, be separated (for instance using a suitable device such as a cyclone separator) from the liquor prior to said second stage, the liquor then being subjected to the second stage of hydrolysis in order to secure greater conversion to terephthalic acid.

Terephthalic acid produced by the process of the present invention may be employed as a monomer in a polymerisation process for example the production of polyalkylene terephthalate without any further purification. Also, if desired, such terephthalic acid may be subjected to further purification such as that conventionally employed in plants for the manufacture of terephthalic acid by the liquid phase oxidation of p-xylene which comprises dissolving the crude terephthalic acid in water at elevated temperature, hydrogenating the aqueous terephthalic acid solution and recrystallising the terephthalic acid from the solution to give purified terephthalic acid suitable for polymerisation with an alkylene glycol.

Terephthalic acid produced by hydrolysis of polyalkylene terephthalate may be used as a feedstock in further processing such as polymerisation with an alkylene glycol either without being mixed with terephthalic acid from an alternative source or preferably in admixture with purified terephthalic acid produced by the liquid phase oxidation of p-xylene.

The terephthalic acid obtained from the process of the invention may be used directly as a feedstock without preliminary drying thereof. For instance, the "wet" terephthalic acid resulting from the hydrolysis process may be slurried with alkylene glycol and polymerised with the glycol, for example in the production of PET bottles. In this event, the terephthalic acid/glycol slurry may be subjected to filtration prior to the polymerisation reaction in order to separate out particulate impurities such as PVC, which will tend to be present in particle sizes larger than the terephthalic acid crystals.

In some instances, it is advantageous to blend terephthalic acid derived by the process of the present invention with crude terephthalic acid derived from the oxidation of paraxylene and purify the blend by dissolution in water, hydrogenation of the resulting aqueous solution and recrystallisation of the terephthalic acid from the solution to produce a purified blend of terephthalic acid derived from separate sources which can be used for polymerisation with an alkylene glycol to produce acceptable quality products, eg having CIE b* values within industry standards for various products.

After separation of terephthalic acid from the liquor following hydrolysis, the liquor my be recycled for use in a subsequent hydrolysis reaction in accordance with the process of the present invention. In this event, the liquor may be treated to recover part of the glycol content thereof and then recycled with added water to effect hydrolysis of a fresh batch of polyalkylene terephthalate.

The invention will now be illustrated by the following non-limiting Examples.

EXAMPLE 1

PET in chip form and demineralised water were mixed to produce a fixture having a PET to Mater ratio of 1:3 and was heated to a temperature (T) for 2 hours in a rocking autoclave so that the mixture was agitated throughout the hydrolysis reaction. After this time the solid terephthalic acid product was separated from the aqueous medium by filtering, drying the solid product and sieving it. This procedure was conducted at constant temperatures of 200°, 220°, 240° and 260° C. The purity of the sieved product was determined by adding an excess of sodium hydroxide solution to a weighed sample of the solid and titrating the solution with hydrochloric acid using an automatic titrator. The first end point occurs at pH 8.3 as the excess hydroxide is titrated. Further acid is then added to titrate the sodium terephthalate solution to give a second end point at around pH 3.7. The amount of acid between the two end points gives a reliable assay of the terephthalic acid content of the sieved product. The results are shown in Table 1.

EXAMPLE 2

The procedure of Example 1 was repeated with the exception that sliced bottle polymer PET was used instead of the chip form PET and runs were conducted at 200° and 220° C. only. The results are shown in Table 1.

EXAMPLE 3

The procedure of Example 2 was repeated with the exception that all runs were conducted at 220° C. but the ratio of PET to water was varied. The results are shown in Table 1.

TABLE 1

| Example | PET:Water | Polymer Type | Temp (°C.) | Time (mins) | Solid TA (%) | Product Purity |
|---------|-----------|--------------|------------|-------------|--------------|----------------|
| 1a | 25:75 | CHIP | 260 | 120 | 33 | 96.5 |
| 1b | 25:75 | CHIP | 240 | 120 | 71 | 98.6 |
| 1c | 25:75 | CHIP | 220 | 120 | 83 | 96.8 |
| 1d | 25:75 | CHIP | 200 | 120 | 92 | 98.3 |
| 2a | 25:75 | BOTTLE | 220 | 120 | 85 | 98.6 |
| 2b | 25:75 | BOTTLE | 200 | 120 | 86 | 91.8 |
| 3a | 25:75 | BOTTLE | 220 | 120 | 85 | 98.6 |
| 3b | 35:65 | BOTTLE | 220 | 120 | 86 | 93.1 |
| 3c | 40:60 | BOTTLE | 220 | 120 | 93 | 99.2 |
| 3d | 45:55 | BOTTLE | 220 | 120 | 93 | 98.2 |
| 3e | 50:50 | BOTTLE | 220 | 120 | 95 | 98.6 |
| 3f | 60:40 | BOTTLE | 220 | 120 | 98 | 99.8 |

In the above Examples, Solid TA refers to the approximate amount of terephthalic acid present in the solid phase at the reaction temperature, expressed as a percentage of the total terephthalic acid produced.

Examples 1 to 3 illustrate that high purity terephthalic acid may be produced by the process of the invention.

EXAMPLE 4

A stainless steel autoclave having a working volume of 25 liters was charged with 16 liters of demineralised water and 8 kg of PET flake. The autoclave was fitted with a paddle stirrer which was operated during the addition of the PET flake to prevent the flake from settling. The autoclave was purged with nitrogen and then heated using a hot oil jacket to 220° C. over a period of 90 minutes with stirring. The temperature was held at 220° C. for 120 minutes with stirring during which time of terephthalic acid formed about 90% is in the solid phase. The vessel was then cooled to 100° C. and the slurry of terephthalic acid in the aqueous medium discharged via a mushroom valve at the base of the reactor through a filter which served to separate the terephthalic acid from the aqueous medium (containing soluble impurities which pass through the filter with the aqueous medium). Both the filter cake formed on the filter and the autoclave were rinsed, the terephthalic acid was reslurried in 15 liters of demineralised water and the slurry was returned to the autoclave where it was heated to 100° C. with stirring for 10 minutes to effect a hot wash. The slurry was again discharged through the filter, the terephthalic acid was recovered and dried in air. The yield obtained was 90% and the product obtained was found to have the following colour characteristics:

a*: −2.33 b*: 4.52 L: 90.4
TA purity: 99.8%

EXAMPLE 5

The procedure of Example 4 was repeated and the terephthalic acid obtained following the hot wash was reslurried once more in 15 liters of demineralised water and the hot washing step was repeated again. The resulting product was found to have the following improved colour characteristics as a consequence of the second hot wash:

a*: −2.21 b*: 2.96 L: 90.3
TA purity: 99.7% This Example illustrates the fact that the second hot wash is effective in removing yellow colour formers to a greater degree.

EXAMPLE 6

A stainless steel autoclave having a working volume of 4 liters was charged with 500 g PET flake, 400 g mono ethylene glycol and 1100 g demineralised water. The autoclave was purged with nitrogen and stirring with a paddle was commenced. The vessel was heated using an electric band heater to 220° C. over a period of 1 hour. A temperature of 220° C. was then maintained for 2 hours and stirring continued throughout this period in order to agitate the reaction mixture and suppress the formation of, and/or comminution of, long needle-shaped crystals of terephthalic acid. In the course of the reaction, of the terephthalic acid produced, an amount in excess of 70% was in the solid phase. The contents of the autoclave were then cooled using a water filled cooling coil in the reactor. The contents of the autoclave (a thick paste) were slurried in a further liter of hot water and the solids filtered off (the filtrate temperature being about 90° C.). This solid was analysed as being about 96% pure terephthalic acid. 15 g of this solid was then washed in 50 g of hot (90° C.) ethylene glycol/water mixture (25% by weight glycol), the slurry filtered hot and the solid rinsed three times in cold water. 12.2 g of solid was recovered and analysed as being substantially 100% pure terephthalic acid.

The TA product obtained was found to have the following characteristics:

|  | L | a* | b* | TA Purity (%) |
|---|---|----|----|---------------|
| Before glycol wash: | 89.52 | −2.35 | +4.20 | 95.9 |
| After glycol wash: | 90.16 | −2.70 | +3.06 | 100 |

EXAMPLE 7

A 2 liter (internal volume) autoclave fitted with an internal glass liner was charged with 60 g PET flake, 48 g mono ethylene glycol and 132 g distilled water. The autoclave was purged with nitrogen before being heated (with rocking agitation) to 220° C. for 2 hours, after which about 90% of the terephthalic acid formed is in the solid phase. The container was cooled and the solid recovered and rinsed in cold water three times. At this stage, the solid was 83.6% pure terephthalic acid. 15 g of this solid was then washed with 50 g of hot (90° C.) ethylene glycol/water mixture (containing 25% by weight glycol) and rinsed three times with cold water. 9.5 g solid was recovered which was analysed as being 97.8% pure terephthalic acid.

The TA product obtained was found to have the following characteristics:

|  | L | a* | b* | TA Purity (%) |
| --- | --- | --- | --- | --- |
| Before glycol wash: | 90.95 | −1.91 | +2.87 | 83.6 |
| After glycol wash: | 89.03 | −2.15 | +4.57 | 97.8 |

EXAMPLE 8

The process of Example 7 was repeated using 60 g PET flake, 60 g ethylene glycol and 120 g distilled water. The terephthalic acid obtained following rinsing was found to be 75.2% pure. After washing 15 g of the solid, using the water/glycol mixture, 10.2 g of 89.9% pure terephthalic acid was recovered.

The TA product obtained was found to have the following characteristics:

|  | L | a* | b* | TA Purity (%) |
| --- | --- | --- | --- | --- |
| Before glycol wash: | 90.54 | −1.84 | +2.76 | 75.2 |
| After glycol wash: | 90.06 | −1.78 | +1.47 | 89.9 |

Examples 6 to 8 demonstrate that the addition of glycol to the hydrolysis reaction my reduce the purity of the initially produced terephthalic acid. However, using a hot wash, a substantial amount of the impurities may be removed. The colour data for Examples 6 and 8 also indicate that the effect of a hot wash is to improve the colour of the terephthalic acid. Example 7 gave a contradictory result, probably due to some glycol from the water/glycol wash remaining on the terephthalic acid and discolouring the latter as it dried.

In each Examples 6 to 8, terephthalic acid purity was determined by direct NaOH titration of a solution containing about 1.2 g of the solid dissolved in 75 ml pyridine to which 75 ml of water was added after dissolution of the solid. An automatic titrator was used and the end point was detected at a measured pH of about 10.2. This techique avoids hydrolysis of low molecular weight esters which would otherwise give different values for the terephthalic acid content of a sample.

EXAMPLE 9

600 g of PVC-containing PET flake (having a chlorine content of about 1000 ppm), obtained from a commercial processor of drop-off scheme PET bottles, was placed in a 4 liter autoclave with 1800 g distilled water and, after purging the vessel with nitrogen, the contents were heated. Tight temperature control was not employed but the contents of the autoclave were at a temperature in excess of 190° C. for 3 hours and at a temperature of 240° C. for about 50 minutes. After cooling the autoclave, the liquor was recovered, the solid material was rinsed to remove glycol generated in the course of the reaction and the solid was then dried and sieved into 4 fractions. The chlorine contents (determined by Neutron activation analysis) of the four fractions are given below together with the chloride content of the liquor (determined by potentiometric titration with silver nitrate).

| Fraction | Chlorine content (ppm) |
| --- | --- |
| >1700 μm | 9740 |
| >710 μm | 1580 |
| >425 μm | 480 |
| <425 μm | 30 |
| Liquor | 614 |

The average chloride content of the solid following removal of the liquor is of the order of 400 ppm. This Example demonstrates that the chloride content tends to reside in the larger particles and that overall the chloride content in the solid is reduced and can be further reduced by rejecting the larger sized particles.

EXAMPLE 10

In order to illustrate the effect of controlling the conditions under which particle formation takes place, the hydrolysis reaction was carried out in a 4 liter autoclave using different degrees of agitation. In each case, the starting mixture comprised water and PET in a ratio of 3:1 (600 g PET, no glycol present in the starting mixture), the reaction was carried out at a temperature of 220° C. the solid (most of which was formed at the reaction temperature) was recovered, rinsed in hot water, dried and then passed through a series of sieves to perform a particle size analysis. In one run, the reaction was carried out without agitation. In second and third runs, agitation was employed but using different agitators. In run 2, the agitator comprised a small (2 cm) paddle stirrer and in run 3 it comprised an anchor stirrer designed to sweep the sides of the liner of the autoclave and which, when run at the same rate as the paddle stirrer, provides more effective agitation than the paddle stirrer. The analysis was performed by plotting the cumulative weight (calculated as a percentage of the total solids and using a logarithmic scale for the cumulative weight) passing through each sieve size. The size through which 50% and 90% of the solids passed was then derived from the graph (by extrapolation where necessary). The results derived were as follows:

|  | Sieve size (50%) | Sieve size (90%) |
| --- | --- | --- |
| Run 1 (no agitation) | 425μ | 850μ |
| Run 2 (paddle agitator) | 375μ | 510μ |
| Run 3 (anchor agitator) | 230μ | 360μ |

Thus, whilst formation of solid phase terephthalic acid at the reaction temperature can be seen to result in relatively small particles (ie without agitation, by extrapolation 90% of the particles are sufficiently small to pass a sieve having a grid 850μ square), by controlling the conditions under which particles formed, the particle size could be reduced even further.

EXAMPLE 11

The procedure as described in Example 10 was also carried out in other vessels provided with agitation namely a 2 liter rocking autoclave (using 60 g PET) and a 5 gallon (UK) vessel (using 8 kg PET) equipped with a paddle/baffle agitation system capable of keeping 7–8 kg of terephthalic acid in suspension and therefore providing good agitation. The results derived from particle size analysis were as follows:

|  | Sieve size (50%) | Sieve size (90%) |
| --- | --- | --- |
| Run 1 (2 litre vessel) | 275μ | 488μ |
| Run 2 (5 gallon vessel) | 210μ | 385μ |

We claim:

1. A process for the production of terephthalic acid from polyalkylene terephthalate, comprising heating a mixture of a solid material containing polyalkylene terephthalate and an aqueous medium to effect hydrolysis of the polyalkylene terephthalate and thereby produce terephthalic acid, the ratio of water to polyalkylene terephthalate in the mixture prior to heating and the conditions under which the hydrolysis reaction is carried out being such that, at the reaction temperature, at least 10% of the terephthalic acid produced is in the solid phase.

2. A process for the production of terephthalic acid from polyalkylene terephthalate, comprising heating a mixture of a solid material containing polyalkylene terephthalate and an aqueous medium to effect hydrolysis of the polyalkylene terephthalate and thereby produce terephthalic acid and alkylene glycol, characterised by, for the purpose of reducing the extent of post-reaction crystallisation necessary to recover the terephthalic acid and reducing the extent of water removal necessary to effect recovery of the glycol:
  (a) the use of a water to polyalkylene terephthalate ratio in the mixture prior to heating and
  (b) the use of hydrolysis reaction conditions such that, at the reaction temperature, at least 10% of the terephthalic acid produced is in the solid phase.

3. A process as claimed in claim 1 or 2 in which at least 20% of the terephthalic acid produced in said hydrolysis reaction is in the solid phase.

4. A process as claimed in claim 1 or 2 in which at least 30% of the terephthalic acid produced in said hydrolysis reaction is in the solid phase.

5. A process as claimed in claim 1 or 2 in which at least 70% of the terephthalic acid produced in said hydrolysis reaction is in the solid phase.

6. A process as claimed in claim 1 or 2 in which at least 80% of the terephthalic acid produced in said hydrolysis reaction is in the solid phase.

7. A process as claimed claim 1 or 2 further comprising separating terephthalic acid from the aqueous glycol-containing liquor remaining following the hydrolysis reaction.

8. A process as claimed claim 7 in which the aqueous medium prior to said hydrolysis reaction contains alkylene glycol.

9. A process as claimed in claim 8 in which the aqueous liquor is processed to separate therefrom at least part of the alkylene glycol present in the mixture prior to the hydrolysis reaction together with that derived from hydrolysis of the polyalkylene terephthalate.

10. A process as claimed in claim 7 in which at least part of said remaining aqueous liquor is recycled, with added water, for use in the hydrolysis reaction of the process.

11. A process as claimed in claim 9 in which the alkylene moiety in the polyalkylene terephthalate corresponds to that in the glycol.

12. A process as claimed in claim 11 in which the alkylene moiety is ethylene.

13. A process for the production of terephthalic acid from polyalkylene terephthalate, comprising:
  heating a mixture of a solid material containing polyalkylene terephthalate, water and alkylene glycol to effect hydrolysis of the polyalkylene terephthalate and thereby produce terephthalic acid, the ratio of water to polyalkylene terephthalate in the mixture prior to heating and the conditions under which the hydrolysis reaction is carried out being such that, at the reaction temperature, at least 30% of the terephthalic acid produced is in the solid phase;
  separating terephthalic acid from the aqueous liquor remaining following the hydrolysis reaction; and
  processing the remaining liquor to separate therefrom alkylene glycol present in the mixture prior to the hydrolysis reaction together with alkylene glycol derived from hydrolysis of the polyalkylene terephthalate.

14. A process as claimed in claim 13 in which at least 70% of the terephthalic acid produced in the hydrolysis reaction is in the solid phase.

15. A process as claimed in claim 1 or 3 in which the water content of the aqueous medium prior to the hydrolysis reaction is at least 85%, more preferably at least 90%, by weight of the liquid phase present.

16. A process as claimed in claim 13 in which the alkylene glycol content of the mixture prior to the hydrolysis reaction is at least 5%, by weight of the liquid phase present.

17. A process as claimed in claim 1 or 13 in which, following hydrolysis, the reaction mixture is cooled with accompanying crystallisation of terephthalic acid and the terephthalic acid so crystallised together with that present in the solid phase under the hydrolysis reaction conditions is separated from the aqueous medium.

18. A process as claimed in claim 1 or 13 in which said separation of the terephthalic acid is effected by hot filtration.

19. A process as claimed in claim 18 in which said hot filtration is carried out at a temperature of at least 60° C.

20. A process according to claim 18 in which the terephthalic acid recovered following said hot filtration is subjected to at least one step comprising hot washing and separation of the washed terephthalic acid from the washing medium.

21. A process as claimed in claim 20 in which the washing medium comprises an alkylene glycol.

22. A process as claimed in claim 1 or 13 including agitating the mixture during heating.

23. A process as claimed in claim 22 including cooling the mixture following the hydrolysis reaction and continuing agitation thereof during cooling.

24. A process as claimed in claim 1 or 13 in which the terephthalic acid recovered from said hydrolysis reaction is blended with terephthalic acid derived directly from the oxidation of paraxylene.

25. A process as claimed in claim 24 in which the blend is subjected to purification by hydrogenation.

26. A process according to claim 1 or 13 in which the mixture is heated to a temperature of at least 190° C. and not exceeding 300° C.

27. A process according to claim 1 or 13 in which the hydrolysis is carried out in the absence of molecular oxygen.

28. A process for the production of terephthalic acid from polyalkylene terephthalate, comprising:

(a) reacting a solid material containing polyalkylene terephthalate with an aqueous medium to hydrolyse the terephthalate to terephthalic acid, the hydrolysis reaction being carried out using a water to polyalkylene terephthalate ratio and reaction conditions which result in at least 10% of the terephthalic acid being produced in the solid phase at the temperature at which the hydrolysis reaction proceeds; and (b) suppressing the formation of and/or comminuting needle-shaped particles of terephthalic acid in the course of the hydrolysis reaction.

29. A process as claimed in claim 28 in which at least a major part of the terephthalic acid is produced in the solid phase at the temperature at which the hydrolysis reaction proceeds.

30. A process as claimed in claim 29 comprising recovering terephthalic acid particles from the reaction mixture, the proportion of solid phase terephthalic acid formed in step (a) and the suppression and/or comminution of step (b) resulting in at least 90% of the particles recovered being sufficiently small to pass a sieve having a grid size no greater than 2 mm square.

31. A process as claimed in claim 30 in which at least 90% of the particles obtained are sufficiently small to pass a sieve having a grid size no greater than 1 mm square.

32. A process as claimed in claim 30 or claim 31 in which the particles of terephthalic acid are recovered after cooling of the reaction mixture whereby a proportion of the recovered particles comprise particles formed during cooling.

33. A process as claimed in claim 32 including suppressing the formation of and/or comminuting needle-shaped particles of terephthalic acid during cooling.

34. A process as claimed in claim 28 in which said suppressing formation of and/or comminuting of needle-shaped particles is effected by agitating the reaction mixture.

* * * * *